United States Patent
Sahin et al.

(10) Patent No.: US 12,329,777 B2
(45) Date of Patent: Jun. 17, 2025

(54) USE OF MUTANT P53 GENE TARGETED LEAD BORATE NANOPARTICLES IN CANCER TREATMENT AND PRODUCTION METHOD OF THESE NANOPARTICLES

(71) Applicant: YEDITEPE UNIVERSITESI, Istanbul (TR)

(72) Inventors: Fikrettin Sahin, Istanbul (TR); Pakize Neslihan Tasli, Istanbul (TR); Oguz Kaan Kirbas, Istanbul (TR); Taha Bartu Hayal, Istanbul (TR); Batuhan Turhan Bozkurt, Istanbul (TR); Berna Bulbul, Balikesir (TR); Seda Beyaz, Balikesir (TR)

(73) Assignee: YEDITEPE UNIVERSITESI, Istanbul (TR)

( * ) Notice: Subject to any disclaimer, the term of this patent is extended or adjusted under 35 U.S.C. 154(b) by 1014 days.

(21) Appl. No.: 17/288,596

(22) PCT Filed: Nov. 8, 2018

(86) PCT No.: PCT/TR2018/050669
§ 371 (c)(1),
(2) Date: Apr. 26, 2021

(87) PCT Pub. No.: WO2020/086014
PCT Pub. Date: Apr. 30, 2020

(65) Prior Publication Data
US 2022/0000910 A1    Jan. 6, 2022

(30) Foreign Application Priority Data
Oct. 25, 2018 (TR) ................. 2018/15980

(51) Int. Cl.
*A61K 33/241* (2019.01)
*A61K 9/14* (2006.01)
*A61K 47/10* (2017.01)
*A61P 35/00* (2006.01)

(52) U.S. Cl.
CPC ............ *A61K 33/241* (2019.01); *A61K 9/14* (2013.01); *A61K 47/10* (2013.01); *A61P 35/00* (2018.01)

(58) Field of Classification Search
CPC ........ A61K 33/241; A61K 9/14; A61K 47/10; A61P 35/00; C01B 35/127
See application file for complete search history.

(56) References Cited

FOREIGN PATENT DOCUMENTS

| CN | 1562840 A | 1/2005 |
|---|---|---|
| CN | 103046113 A | 4/2013 |
| CN | 105568378 A | 5/2016 |
| JP | 2005300232 A | 10/2005 |
| WO | 2011022350 A1 | 2/2011 |
| WO | 2012009406 A2 | 1/2012 |
| WO | 2012104831 A1 | 8/2012 |
| WO | 2013014538 A2 | 1/2013 |

OTHER PUBLICATIONS

Jun Fang, et al., The EPR effect: Unique features of tumor blood vessels for drug delivery, factors involved, and limitations and augmentation of the effect, Advanced Drug Delivery Reviews, 2011, pp. 136-151, 63.
Paula Garcia Calavia, et al., Targeted photodynamic therapy of breast cancer cells using lactose-phthalocyanine functionalized gold nanoparticles, Journal of Colloid and Interface Science, 2018, pp. 249-259, 512.
Azadeh Hekmat, et al., The Effects of Silver Nanoparticles and Doxorubicin Combination on DNA Structure and Its Antiproliferative Effect Against T47D and MCF7 Cell Lines, J. Biomed. Nanotechnol., 2012, pp. 968-982, vol. 8 No.6.
Douglas Hanahan, et al., The Hallmarks of Cancer, Cell, 2000, pp. 57-70, vol. 100.
Douglas Hanahan, et al., Hallmarks of Cancer: The Next Generation, Cell, 2011, pp. 646-674, 144.

*Primary Examiner* — Robert A Wax
*Assistant Examiner* — Quanglong N Truong
(74) *Attorney, Agent, or Firm* — Bayramoglu Law Offices LLC

(57) ABSTRACT

Use of nano-sized lead borate compounds for treatment purposes due to their selective anticancer activity on p53 mutant breast cancer cell line, T47D is disclosed. The method of synthesizing nano-sized lead borates of the present invention comprises the steps of preparing a borate buffer solution by sodium hydroxide and boric acid, dissolving lead nitrate (and preferably PEG) in distilled water by stirring, mixing the borate buffer solution with the lead nitrate (and preferably PEG) solution, washing the resulting solution with distilled water and drying to remove the impurities.

15 Claims, 3 Drawing Sheets

USE OF MUTANT P53 GENE TARGETED LEAD BORATE NANOPARTICLES IN CANCER TREATMENT AND PRODUCTION METHOD OF THESE NANOPARTICLES

CROSS REFERENCE TO THE RELATED APPLICATIONS

This application is the national phase entry of international Application No. PCT/TR2018/050669, filed on Nov. 8, 2018, which is based upon and claims priority to Turkish Patent Application No. 2018/15980, filed on Oct. 25, 2018, the entire contents of which are incorporated herein by reference.

FIELD OF THE INVENTION

The present invention relates to use of nano-sized lead borate compounds for treatment purposes due to their selective anticancer activity on p53 mutant breast cancer cell line, T47D.

BACKGROUND OF THE INVENTION

Lead borates (PbxByOzHt-PbxByOz), have attracted great deal of interest of the researches in the recent years due to their superior optical and photoelectric properties in addition to the ability of being used both as a catalyst and a neutron-gamma ray capture material and they have been tried to be synthesized using various synthesis methods. However, it is observed that the health effects and biological applications of these compounds have not been examined so far. Some of the lead borate compounds synthesized using the conventional solid-state, sol-gel and solvothermal synthesis methods in the literature are as follows: $PbB_4O_7$, $Pb(BO_2)_2 \cdot H_2O$, $Pb_6B_{10}O_{21}$, $Pb_3B_{10}O_{18} \cdot 2H_2O$, $Pb_2[B_5O_9]OH \cdot H_2O$, $Pb_5B_3O_8(OH)_3 \cdot H_2O$, $Pb_6B_{12}O_{24} \cdot H_2O$, $Pb_2B_3O_{5.5}(OH)_2$, $[Pb_3(B_3O_7)] \cdot NO_3$, $Pb_6B_{11}O_{18}(OH)_9$ and $Pb_6B_6O_{15}$.

As it is known, many physical properties of the materials change and acquire a higher quality when moving from microsizes to nanosizes. Therefore the nano-size synthesis of lead borate compounds has gained importance, but the studies on the synthesis of these compounds in the literature remain very limited. One of these studies is obtaining lead borate by the microwave co-precipitation method which is disclosed in the Chinese patent application no. CN1562840. In this synthesis, sodium borate and lead nitrate solutions were mixed in the appropriate stoichiometric proportions in the presence of 2-ethylhexyl sulfosuccinate and the resulting mixture was subjected to microwave rays in a laboratory type microwave at a temperature of 35-45° C. for 1.5-2 hours with a power of 500 W. The obtained products were washed with distilled water and ethanol and then dried in an oven at 60° C. for 10 hours to remove the impurities. The second study is about synthesizing nanosized $Pb_3B_{10}O_{16}(OH)_4$ compound by means of solvothermal method which is disclosed in Chinese patent application no. CN105568378. In this synthesis, lead acetate and boric acid solutions were mixed in appropriate stoichiometric ratios in the presence of pyridine and the pH of the medium was adjusted using ammonia solution. The resulting mixture was transferred to an autoclave and heated at 230 degrees for 12 hours. The obtained products were washed with distilled water and ethanol and heated at 60 degrees for 12 hours.

Cancer is the general name of the diseases resulting from uncontrolled growth and division of the cells. While the cancerous cells can be formed in most tissues of the body, the cancerous cells that are formed can metastasize to different parts of the body by means of blood. Cancer has six basic hallmarks. These are as follows:

11. Synthesizing growth factors themselves,
12. Evading the growth inhibitory signals,
13. Finding other ways for survival to resist programmed cell death,
14. Having capability for unlimited proliferation,
15. Ability to produce new blood vessels (angiogenesis) for sustenance and
16. Invasion and metastasis to other tissues through blood vessels [1].

Eleven years after identification of these six hallmarks, an updated article was published by Hanahan and Weinberg in which they increased the number of cancer hallmarks to ten. The added four hallmarks are as follows:

17. Having irregular metabolic pathways,
18. Having instable genome open to mutations,
19. Avoiding immune system and
20. Tumor promoting inflammation [2].

These ten traits are the main cause of cancer-related deaths, and cancer is statistically the second most common cause of death after cardiovascular diseases. Billions of dollars are spent every year in order to find a cure for cancer, which is one of the issues that attract the most attention of the scientists worldwide, and to treat patients, Although there are only 250 cancer drugs supported by NCI (National Cancer Institute), all of these drugs have 23 known side effects.

In a study conducted by Paula García Calavia et al. in 2018, the photodynamic effect of lactose-phthalocyanine functionalized gold nanoparticles on breast cancer was investigated. Lactose, the carbohydrate in the said study, was used for both stabilizing the gold nanoparticles and targeting the breast cancer cells via galectin-1 receptor. MDA-MB-231 breast adenocarcinoma cell line and healthy breast epithelium MCF-10A were compared, and as a result, it was observed that gold nanoparticles selectively killed the adenocarcinoma cell line with overexpression of galectin-1 receptor, but had no effect on MCF-10A cell line [3].

In an article published by Hekmat A. et al. in 2012, the effects of combinations of silver nanoparticles and doxorubicin on T47D and MCF-7 breast cancer cell lines were shown by comparing with human endometrial stem cells. It was observed that use of combination of 0.3 μM doxorubicin and 10 μM silver nanoparticle on the T47D cell line resulted in a death rate of 60%. In the MCF-7 cell line, the death rate was 49% as a result of the same combination [4].

Nanotechnological products are about one to ten thousand times smaller in size than a cell and with this feature thereof, they are similar to biological molecules such as receptors or some enzymes. Thanks to their small size, the nanoparticles can easily interact with many molecules within and/or outside the cell. The nanoparticles, which are smaller than twenty nanometers, can easily come out of the blood vessels and easily move to any part of the body (EPR effect—enhanced permeability and retention), and this ease of access to any and all parts of the body has a great importance since it provides the potential of identifying the cancer cells and leaving the treatment thereof completely to the nanoparticle. However, the percentage of the EPR effect may decrease in some types of cancers due to changes in the permeability of the blood vessels [5]. Moreover, identification of the cancerous cell is essential as a result of this ease of access. Otherwise the nanoparticles will also kill the healthy cells together with the cancerous cells. In this respect, designing nanoparticles suitable for the patient is important.

Nanoparticle formulation studies attract the attention and interest of researchers because they allow improvement of the current methods in the treatment of cancer.

Surgical operation and/or chemotherapy are frequently used to treat cancer. While surgical operation yields a complete and effective outcome in some cases; usually, a chemotherapeutic drug is administered after the operation against the possibility of presence of cancerous cells that will survive and trigger cancer formation in the long term. Mostly, chemotherapy causes a number of side effects by damaging the healthy cells as well as the cancerous cells. Cells with high proliferation rates in the body are most affected by chemotherapy, which are the hair cells, blood cells produced in the bone marrow and the digestive system cells. The side effects frequently observed after chemotherapy are as follows:

Fatigue: Although it is mostly caused by the anemia resulting from the fact that the blood cells are affected, the cause may also be psychological.

Nausea and Vomiting: While it may be due to sensitivity to the drugs, it may have psychological causes.

Hair Loss: Loss of hair which is adversely affected by chemotherapy due to their rapidly growing cells is one of the most significant reasons for the patients to get depressed.

Decrease of Blood Values: The bone marrow getting affected by chemotherapy results in a significant decrease in blood cells. Since sufficient amount of oxygen cannot be supplied to the tissues as a result of this decrease, many adverse effects such as weakening of the immune system and difficulty in blood clotting can be observed.

Mouth sores: Chemotherapy drugs may sometimes cause inflammatory sores in the mouth. During the treatment, the patients should avoid extremely hot or cold drinks and pay utmost attention to their oral hygiene.

Diarrhea and Constipation: Diarrhea or constipation can be observed as a result of the response of the cells of the digestive system against different chemotherapeutic agents. This situation, whose effects can mostly be reduced via diet, may in some cases result in severe diarrhea requiring intravenous fluid intake.

Skin and Nail Changes: Chemotherapeutic drugs have side effects such as darkening of the skin color, skin peeling, reddening or dry skin. Easy breakage of nails or darkening of their color can also be observed. Particular attention should be paid to peeling of the skin, as it will cause open wounds in immunocompromised patients.

Sleeping Problems: Although it usually occurs due to psychological reasons, failure of the body to rest particularly during chemotherapy treatment process both reduces the effect of chemotherapy and further disrupts the mental health of the patient.

In order to increase the success of the treatment, the requirement to use chemotherapy in combination with both surgical and other methods and the abundance and unpredictability of its side effects varying from patient to patient have led scientists to seek new treatment methods. Nanoparticles have become prominent in the studies commenced in order to improve the current treatment methods and to reduce the side effects.

In addition to all of these, in the current art, nanoparticles are either used in combination with a known chemical—wherein the said chemicals can selectively kill the cancer even if the nanoparticle is not used, here, the impact is aimed to be enhanced—or a targeting is performed by glucose supplement to enable the cells to recognize the nanoparticles. Since need for glucose is common for all cells, being able to kill more cancer cells only proportionally will not cause damage to the healthy cells. Furthermore, as mentioned above, due to the EPR effect of many nanoparticles, the nanoparticles that can enter in an uncontrolled manner into non-cancerous cells can be dangerous to the health of these cells.

Japanese patent document no. JP2005300232, an application in the state of the art, discloses application of positron emission tomography using aerogel and a method of producing the said aerogel. The objective of the present invention is to provide a positron emission tomography that enables to locate the position of abnormal tissues such as cancer cells with high accuracy. One of the raw materials used in aerogel production is lead oxides and for this purpose a lead salt belonging to a group also including lead borate is used.

International patent application no. WO2011022350, an application in the state of the art, discloses pharmaceutically acceptable zinc nanoparticles for the treatment of infections and cancer. Zinc nanoparticles have cores comprising elemental zinc without significant amounts of other metals or metal oxides. Another use of the zinc nanoparticles of the present invention is diagnostics and imaging. Zinc nanoparticles have an inherent auto-fluorescent capacity and thus can be used to image sites such as infections and tumors. Because it is useful in situations such as X-ray imaging, an ion selected from a group also including lead (II) can be used.

Chinese patent application document no. CN103046113, an application in the state of the art, discloses compound lead borate and nonlinear optical crystal of lead borate, and preparation method thereof. The lead borate compound has a chemical formula of $Pb_4O(BO_3)_2$ and a molecular weight of 962.38, and is synthesized by using a solid phase reaction method. The molar ratio of lead and boron in the compound is 2:1 and the lead-containing compound is lead carbonate, lead nitrate, lead oxide, lead acetate or lead oxalate; and the boron-containing compound is boric acid or boron oxide.

It is seen that there is no publication or patent in the literature regarding the effect of the nano-sized lead borate compounds of the present invention on cancer and associated physiological disorders.

SUMMARY OF THE INVENTION

The objective of the present invention is to use the nano-sized lead borate compound in the treatment process due to its selective toxic effect on cancer cells.

Another objective of the invention is to synthesize the nano-sized lead borate compound by using the buffered-precipitation synthesis method for the first time.

A further objective of the invention is to enable these compounds to have a size of less than 100 nm in order to use them in in vivo biological applications.

Another objective of the invention is to use a synthesis method which is much easier, economical and suitable for fabrication in comparison to the hydrothermal/solvothermal and microwave precipitation synthesis methods due to the fact that it can be carried out without any need for high temperature, long reaction times, high pressure and any kind of irradiation.

DETAILED DESCRIPTION OF THE INVENTION

"Use of mutant p53 gene targeted lead borate nanoparticles in cancer treatment and production method of these nanoparticles" developed to fulfill the objective of the present invention is illustrated in the accompanying figure, in which.

Figure 1A:
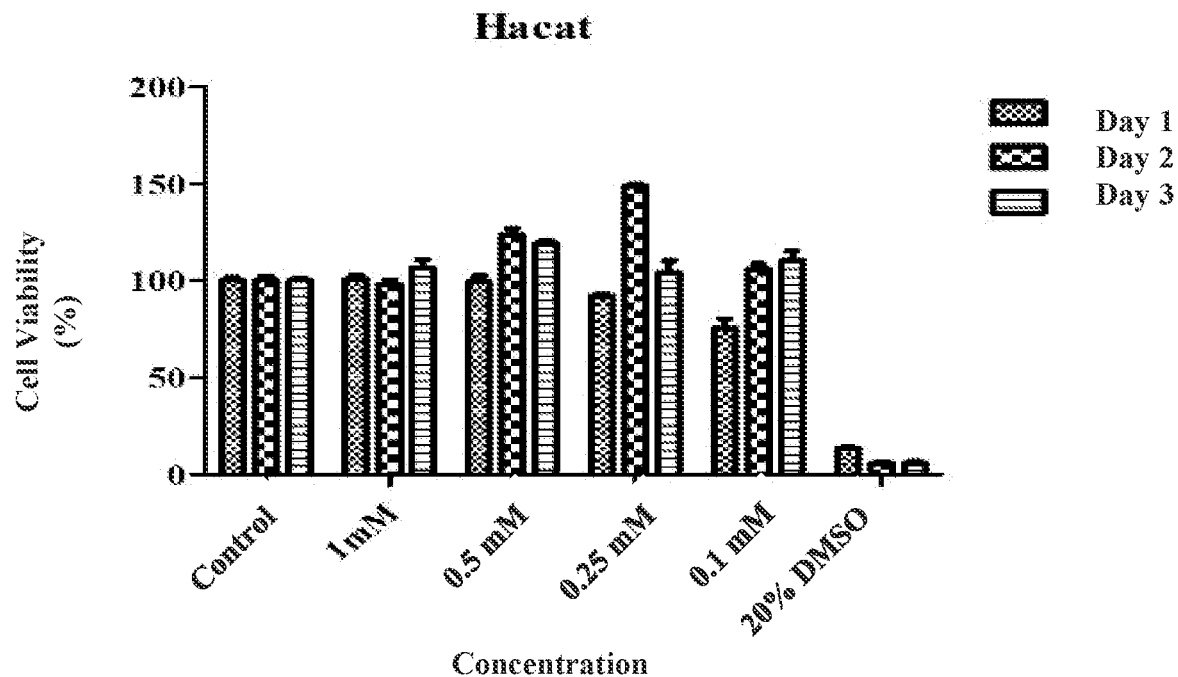
FIG. 1A is the graphical representation of the effect of variable concentrations of nano-sized lead borate on viability in Hacat (Healthy Control Keratinocyte) cells.
Figure 1B:
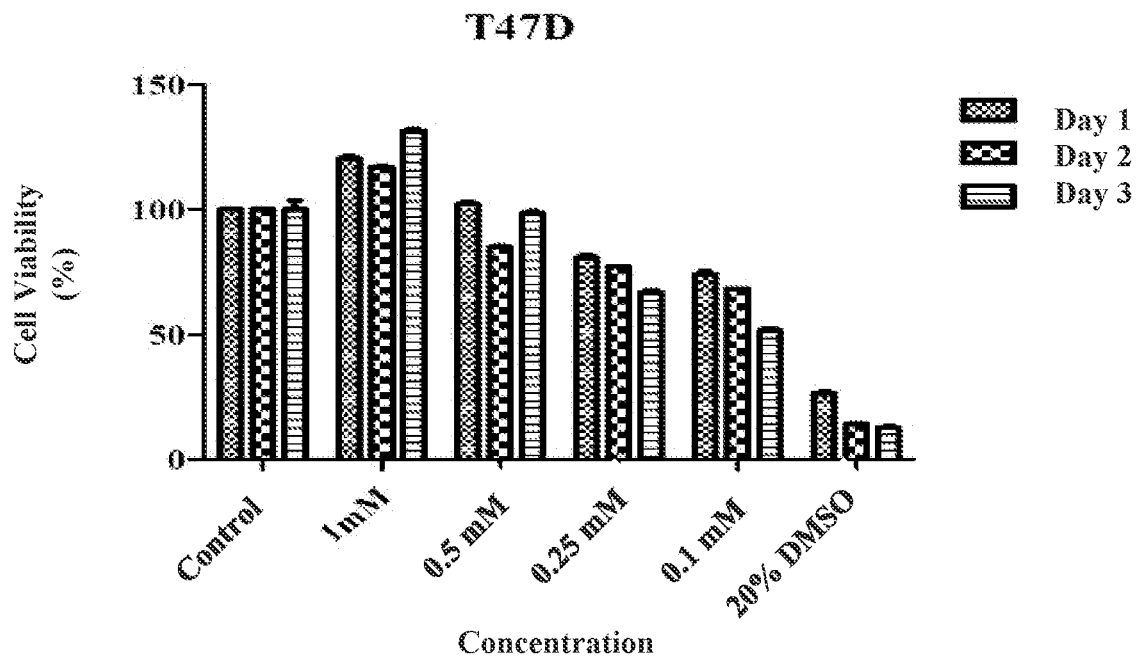
FIG. 1B is the graphical representation of the effect of variable concentrations of nano-sized lead borate on viability in T47D (Breast Cancer) cells.
Figure 1C:
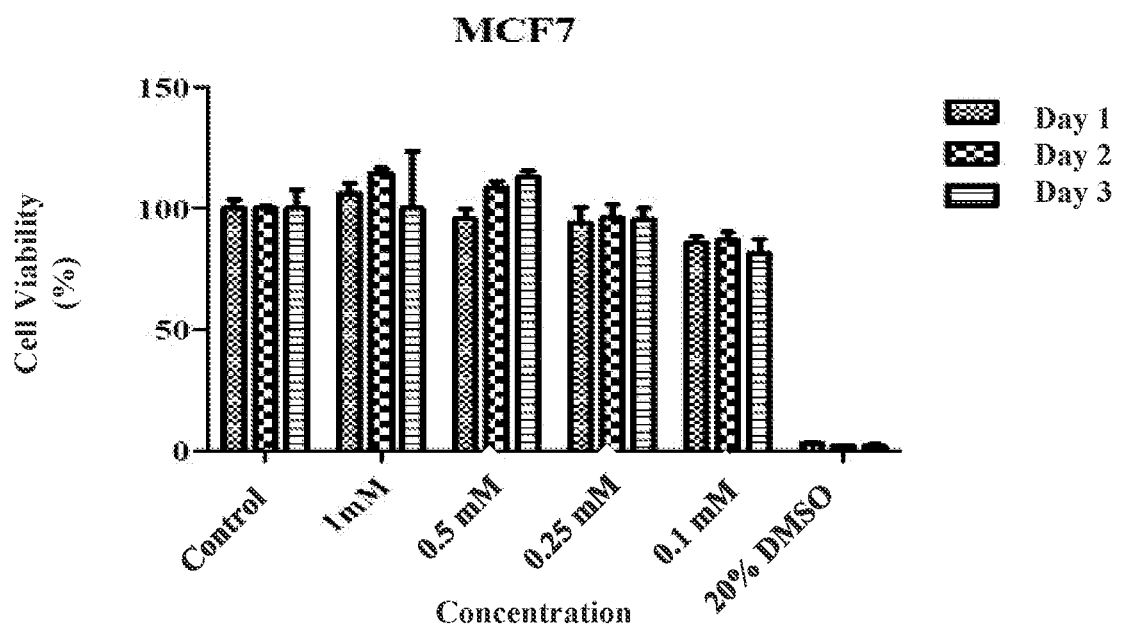
FIG. 1C is the graphical representation of the effect of variable concentrations of nano-sized lead borate on viability in MCF7 (Breast Cancer) cells.
Figure 1D:
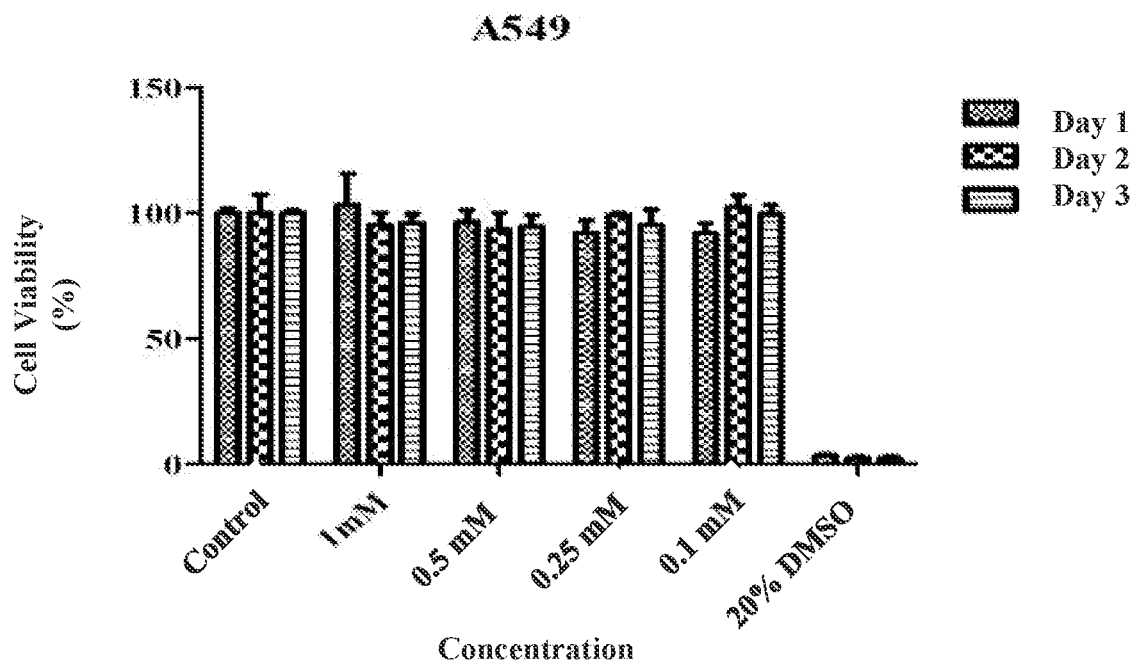
FIG. 1D is the graphical representation of the effect of variable concentrations of nano-sized lead borate on viability in A549 (Lung Cancer) cells.
Figure 2:
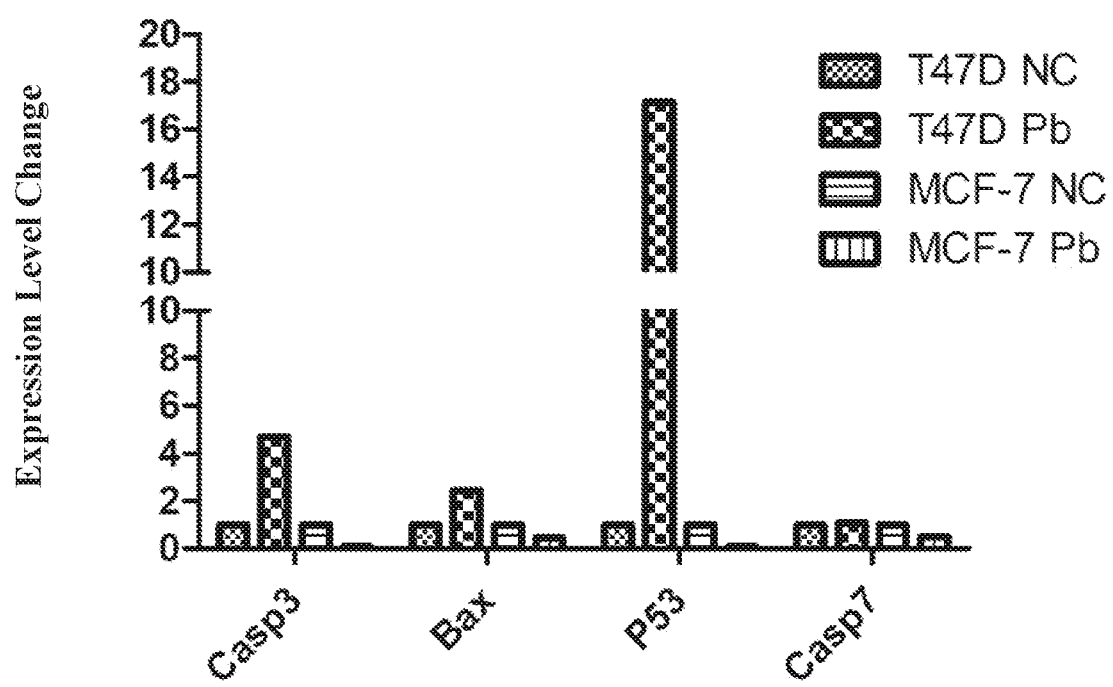

FIG. 2 is a representation of the gene expression change of the T47D cell line having p53 mutation and the MCF7 cell line not having p53 mutation following treatment with lead nanoparticle via real-time polymerase chain reaction. (The results were determined upon being normalized in terms of the controls of the cells not involving nano-particle application and the expression levels of the GAPDH gene which can also be referred to as the guardian gene.)

The present invention relates to nano-sized lead metaborate compounds used for the treatment of cancer due to their selective toxic effect on cancer cells. Within the scope of the present invention, due to their selective anti-cancer effect (toxic effect) on the p53 mutant breast cancer cell line, T47D, nano-sized lead borate compounds are used for the purpose of treatment of these cancerous cells.

The synthesis of nano-sized (below 100 nm) lead borate compounds developed for use in the cancer treatment process In the scope of the invention is carried out under room conditions by means of the buffered precipitation method. The steps of this synthesis method are as follows:

4—Sodium hydroxide and boric acid are dissolved and mixed with each other in a stoichiometric ratio of 1:2 in distilled water, and the borate buffer (NaOH/H$_3$BO$_3$ buffer solution) having a pH value of 9 to 9.5 and having the ability to maintain the pH value of the reaction medium within this range is prepared.

5—Lead nitrate (and preferably PEG (400 to 20000 Da)) is dissolved again in 200 ml of distilled water in a separate beaker in a stoichiometric ratio of 1:1.5. Lead nitrate (and preferably PEG) solution and borate buffer solution are stirred for 30 minutes at 2000 rpm under a mechanical stirrer.

6—The Obtained product is washed 4 times with distilled water and then dried at 60° C. for 24 hours to remove the impurities.

PEG is a biocompatible surfactant. In the method described above, it is also possible to carry out the reaction without the use of surfactants such as PEG. In this case, only 10 mmol of lead nitrate is dissolved in 20 ml of water in a beaker. The purpose of using PEG in the reaction is to obtain lead borate nanoparticles having smaller particle sizes.

The particle sizes of the nano-sized lead borate compounds synthesized according to the invention are below 100 nm. The particle sizes below 100 nm allow these compounds to be used in in vivo biological applications.

The synthesis method used is a method which is much easier, economical and suitable for fabrication in comparison to the hydrothermal/solvothermal and microwave precipitation synthesis methods due to the fact that it can be carried out without any need for high temperature, long reaction times, high pressure and any kind of irradiation.

PEG (Polyethylene glycol) added to the medium is a biocompatible surfactant. It allows the obtained particles to be obtained in smaller sizes (50 nm and below) and to be easily dispersed in water. In order to be able to use lead borate compounds in biological applications and to obtain smaller nanoparticles, PEGs and other biocompatible surfactants with different molecular weights can be used during or after the reaction.

This buffered-precipitation method for forming the nanoparticle according to the invention is a novel precipitation method for the synthesis of only metal borates obtained by improvement of certain parts of the conventional precipitation method previously known in the literature. The most important feature of this method is the ability of the sodium hydroxide/boric acid buffer used as the borate source to maintain the pH value of the medium between 9 and 9.5 throughout the reaction. This synthesis method can be used not only to obtain lead borate but also to obtain all other (+2) and (+3) charged metal borates. The metals of the other metal borate compounds that can be synthesized using this synthesis method are as follows: $Ca^{+2}$, $Mn^{+2}$, $Ni^{+2}$, $Co^{+2}$, $Cu^{+2}$, $Zn^{+2}$, $Sr^{+2}$, $Ba^{+2}$, $Sc^{+3}$, $Fe^{+3}$, $Cr^{+3}$, $Al^{+3}$, $Y^{+3}$, $La^{+3}$, $Ce^{+3}$, $Pr^{+3}$, $Nd^{+3}$, $Sm^{+3}$, $Eu^{+3}$, $Gd^{+3}$, $Tb^{+3}$, $Dy^{+3}$, $Ho^{+3}$, $Er^{+3}$, $Tm^{+3}$, $Yb^{+3}$, $Lu^{+3}$, $Bi^{+3}$, $Tl^{+3}$. The examples given here are examples of the other metal borate examples that can be obtained by this synthesis method.

Experimental Studies

Cytotoxicity Experiment

The effect of the prepared nanoparticles on cell viability was determined by using the MTS (material testing systems) method given in the literature. The molecules used in the product were prepared alone or in combination in the medium and applied on T47D (Breast Cancer), MCF7 (Breast Cancer), A549 (Lung Cancer) and Hacat (Healthy Control Keratinocyte) cells which were seeded on 96-well culture plates by counting at a concentration of 4000 cells per each well. The response of the cells to toxicity of the molecules was determined by measuring cell viability for 3 days. Cell viability was determined by using a method called MTS which measures mitochondrial dehydrogenase enzyme activity of the cell. The MTS substance added onto the cells together with the medium results in colored formazan crystals formation as an indicator of cell viability. The resulting color change was evaluated based on the absorbance measurement by using ELISA plate reader. The obtained results were analyzed.

Real Time Polymerase Chain Reaction

Real-time polymerase chain reaction assay is performed to observe the changes in the gene levels of the cells treated with nanoparticles. These changes are both at morphological level and gene expression level. The primers that were used were designed using Primer BLAST software (The National Center for Biotechnology=NCBI). Total RNAs were isolated from the cells on which gel combination was applied and cDNA was synthesized. The synthesized cDNAs were mixed with primers in Fermentas Maxima SYBR Green mixture product such that the final volume will be 20 μl and the expression levels of the genes were analyzed by using BIO-RAD device.

What is claimed is:

1. A method for synthesizing nano-sized lead borate compounds, wherein the nano-sized lead borate compounds are used for a treatment of a cancer due to a selective toxic effect of the nano-sized lead borate compounds on cancer cells; the method comprising the steps of:

dissolving and mixing sodium hydroxide and boric acid with each other in distilled water to obtain a borate buffer solution a NaOH/H$_3$BO$_3$ buffer solution, dissolving lead nitrate in distilled water in a separate beaker by a stirring to obtain a lead nitrate solution, mixing the lead nitrate solution with the borate buffer solution to obtain a product, washing the product with distilled water to obtain a washed product and then drying the washed product to remove impurities.

2. The method for synthesizing the nano-sized lead borate compounds according to claim 1, wherein the method is implemented by a buffered precipitation.

3. The method for synthesizing the nano-sized lead borate compounds according to claim 1, wherein the sodium hydroxide and the boric acid are mixed in a stoichiometric ratio of 1:2 in the distilled water.

4. The method for synthesizing the nano-sized lead borate compounds according to claim 1, wherein the borate buffer solution maintains a pH value of a reaction medium between 9 and 9.5.

5. The method for synthesizing the nano-sized lead borate compounds according to claim 1, wherein, in the step of mixing the lead nitrate solution and the borate buffer solution, the lead nitrate solution and the borate buffer solution are stirred for 30 minutes at 2000 rpm under a mechanical stirrer.

6. The method for synthesizing the nano-sized lead borate compounds according to claim 1, wherein, in the step of washing the product and drying the washed product to remove the impurities, the product is washed 4 times with distilled water and then the washed product is dried at 60° C. for 24 hours.

7. The method for synthesizing the nano-sized lead borate compounds according to claim 1, wherein 10 mmol of the lead nitrate is dissolved in 20 ml of the distilled water.

8. The method for synthesizing the nano-sized lead borate compounds according to claim 1, wherein, in the case that the lead nitrate is dissolved in the distilled water, PEG (Polyethylene Glycol) is also dissolved in the distilled water together with the lead nitrate.

9. The method for synthesizing the nano-sized lead borate compounds according to claim 8, wherein the lead nitrate and the PEG, wherein the PEG is between 400 to 20000 Da, are dissolved in 200 ml of the distilled water in a stoichiometric ratio of 1:1.5.

10. The method for synthesizing the nano-sized lead borate compounds according to claim 1, wherein, due to the selective toxic effect of the nano-sized lead borate compounds on a p53 mutant breast cancer cell line, T47D, the nano-sized lead borate compounds are used for the treatment of cancerous cells of the T47D.

11. The method for synthesizing the nano-sized lead borate compounds according to claim 2, wherein, in the case that the lead nitrate is dissolved in the distilled water, PEG is also dissolved in the distilled water together with the lead nitrate.

12. The method for synthesizing the nano-sized lead borate compounds according to claim 3, wherein, in the case that the lead nitrate is dissolved in the distilled water, PEG is also dissolved in the distilled water together with the lead nitrate.

13. The method for synthesizing the nano-sized lead borate compounds according to claim 4, wherein, in the case that the lead nitrate is dissolved in the distilled water, PEG is also dissolved in the distilled water together with the lead nitrate.

14. The method for synthesizing the nano-sized lead borate compounds according to claim 5, wherein, in the case that the lead nitrate is dissolved in the distilled water, PEG is also dissolved in the distilled water together with the lead nitrate.

15. The method for synthesizing the nano-sized lead borate compounds according to claim 6, wherein, in the case that the lead nitrate is dissolved in the distilled water, PEG is also dissolved in the distilled water together with the lead nitrate.

* * * * *